United States Patent
Connelly et al.

(10) Patent No.: US 10,945,428 B2
(45) Date of Patent: Mar. 16, 2021

(54) PRESERVATION OF CELLULAR COMPONENTS FROM CELLS WITH A PRESERVATIVE

(71) Applicant: Menarini Silicon Biosystems, Inc., San Diego, CA (US)

(72) Inventors: Mark Connelly, Doylestown, PA (US); Chandra Galla Rao, Princeton Junction, NJ (US); Denis Smirnov, Media, PA (US)

(73) Assignee: Menarini Silicon Biosystems S.p.A., Bologna (IT)

( * ) Notice: Subject to any disclaimer, the term of this patent is extended or adjusted under 35 U.S.C. 154(b) by 0 days.

(21) Appl. No.: 15/448,878

(22) Filed: Mar. 3, 2017

(65) Prior Publication Data

US 2018/0055041 A1    Mar. 1, 2018

Related U.S. Application Data

(60) Provisional application No. 62/303,886, filed on Mar. 4, 2016.

(51) Int. Cl.
| | | |
|---|---|---|
| *A01N 1/02* | (2006.01) |
| *A01N 1/00* | (2006.01) |
| *C07C 59/147* | (2006.01) |
| *C12M 1/00* | (2006.01) |
| *G01N 33/50* | (2006.01) |

(52) U.S. Cl.
CPC ............. *A01N 1/0226* (2013.01); *A01N 1/00* (2013.01); *C07C 59/147* (2013.01); *C12M 47/04* (2013.01); *G01N 33/5005* (2013.01)

(58) Field of Classification Search
CPC ...... A01N 1/0226; A01N 1/00; C07C 59/147; C12M 47/04
See application file for complete search history.

(56) References Cited

U.S. PATENT DOCUMENTS

| | | | | |
|---|---|---|---|---|
| 5,422,277 | A * | 6/1995 | Connelly | G01N 1/30 435/29 |
| 5,911,917 | A * | 6/1999 | Masters | A01N 3/00 252/400.1 |
| 2006/0008807 | A1 | 1/2006 | O'Hara et al. | |
| 2006/0194192 | A1 | 8/2006 | Rao et al. | |
| 2011/0008963 | A1 * | 1/2011 | Liu | B82Y 30/00 438/680 |
| 2011/0027771 | A1 * | 2/2011 | Deng | C12Q 1/6806 435/2 |
| 2016/0081328 | A1 * | 3/2016 | Thatte | A01N 1/0226 435/2 |

FOREIGN PATENT DOCUMENTS

| | | |
|---|---|---|
| EP | 0083126 B1 | 7/1983 |
| WO | WO 03/018757 A2 | 3/2003 |
| WO | WO-2014183134 A1 * | 11/2014 ........... A01N 1/0226 |
| WO | WO 2015058206 | 4/2015 |

OTHER PUBLICATIONS

Sigma Product Information Sheet, EDTA (Year: 2019).*

* cited by examiner

*Primary Examiner* — Ruth A Davis
(74) *Attorney, Agent, or Firm* — Foley & Lardner LLP

(57) ABSTRACT

This invention relates to a preservative solution and a method to preserve whole blood for cellular and molecular analysis.

20 Claims, 3 Drawing Sheets

PRESERVATION OF CELLULAR COMPONENTS FROM CELLS WITH A PRESERVATIVE

RELATED APPLICATIONS

This application claims priority to a U.S. Provisional Application 62/303,886, entitled Preservation of Circulating Tumor Cell RNA with a Whole Blood Preservative filed on Mar. 4, 2016.

BACKGROUND

Rare cells including but not limited to circulating tumor cells ("CTC") and circulating multiple myeloma cells are found in whole blood and have been used to evaluate patients for cancer. The commercial device CELL-SEARCH® is an FDA regulated device that is sold in many countries to isolate rare cells such as CTCs and CMMCs. This device isolates the rare cells from blood and phenotypically identifies the type of cell that is present using imaging and fish analysis. In addition in some cases the number of cells has been used to indicate whether a patient's cancer is getting worse or in remission. With the availability of genomic analysis, there is a desire not only to phenotypically identify cells but to extract the DNA and RNA from isolated rare cells and evaluate the genotype of such rare cells.

Rare cells are known to be fragile and the isolation of them from whole blood is a complex task. Often blood is extracted from patients and sent to labs. If such blood is not preserved, no rare cells will be isolated. There are known whole blood preservatives such as Cyto-Chex™ and CELL-SAVE® (manufactured by Streck Laboratories Inc. and Janssen Diagnostics Inc., respectively) as well as EDTA, formaldehyde, glutaraldehyde that are used to preserve CTCs in whole blood for a number of days. However, when one wants to extract nucleic acids from isolated rare cells the cells that are preserved with those preservatives have lower yields of isolated nuclei acids. Therefore it would be beneficial to invent a preservative that allows for higher yields of isolated nucleic acids. This need is met by the following invention

DETAILED DESCRIPTION OF THE INVENTION

Figure 1:
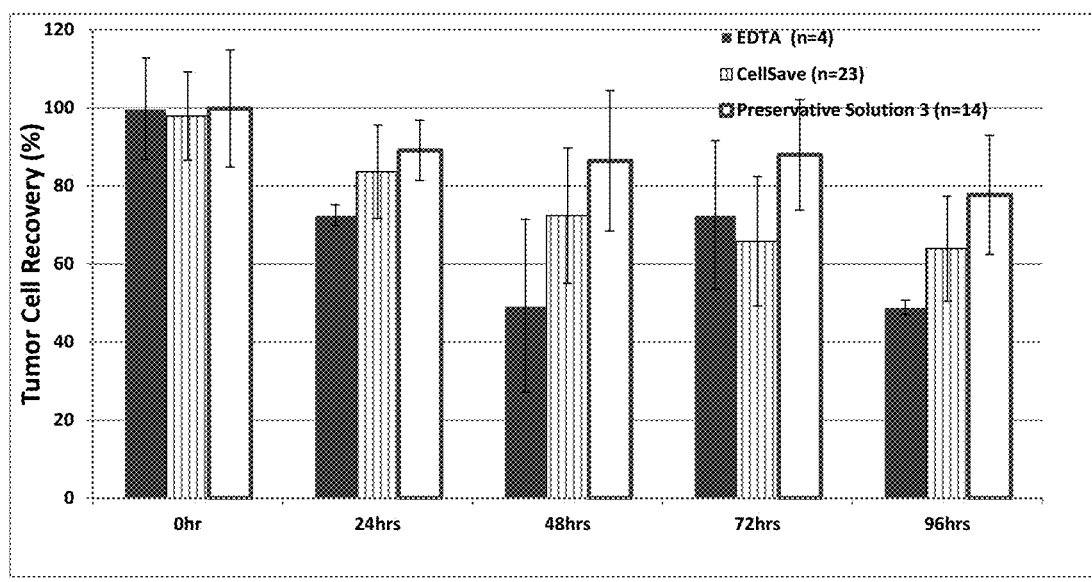
FIG. 1 shows tumor cell recovery as a function of time with different preservatives.

The invention includes a reagent for preserving cells from a biological sample for subsequent isolation of cellular components comprising an effective amount of glyoxal. Examples of cells include but are not limited to red blood cells, white blood cells, platelets, B-Cells, T-cells, subsets of immune cells and rare cells. The preferred cells are B-cells, T-cells and rare cells. The term "rare cells" means a cell, a small cluster of cells, or a class of cells and their associated events that are not readily and reliably detected, or accurately quantified, in biological samples without some form of positive or negative selection enrichment or concentration being applied to the sample. Examples of rare cells include but are not limited to circulating tumor cells (CTC), circulating melanoma cells (CMC), circulating endothelial cells (CEC), circulating multiple myeloma cells (CMMC), circulating fetal cells, antigen-specific T cells, acute myeloid leukemia stem cells, and dendritic cells. The preferred rare cells circulating tumor cells (CTCs), circulating multiple myeloma cells ("CMMCs"), and circulating myeloma cells ("CMCs"). The particularly preferred cells are circulating tumor cells (CTCs). The term "biological sample" means naturally occurring extracts of a patient. Examples of such extracts include but are not limited to whole blood, bone marrow, urine, pleural effusions, saliva, lymph node fluid, and plasma. The preferred biological samples are whole blood and bone marrow, the particularly preferred biological sample is whole blood.

The term cellular components refers to constituents of cells, including but not limited to exosomes, mircrovesicles, and nucleic acids. The preferred cellular components are exosomes, and nucleic acids, most preferably nucleic acids. The term "nucleic acid" includes DNA, RNA and all types thereof. With respect to DNA types of DNA include but are not limited to chromosomal, mitochondrial and pathogen-derived. With respect to RNA, types of RNA non-coding and coding RNA, mRNA, tRNA, incRNA, rRNA, micro RNA, siRNA, snoRNA, piRNA, tsRNA, and srRNA. The preferred nucleic acid is RNA, and its preferred types are, tRNA, rRNA, and mRNA.

The "effective amount" glyoxal is from about 0.1% percent of the reagent to about 0.5% more preferably about 0.2%.

The reagent may comprise additional agents including but not limited to phosphates such as sodium phosphate dibasic heptahydrate, and potassium phosphate; salts such as sodium chloride, potassium chloride, disodium salt dihydrate; bases such as sodium hydroxide and calcium hydroxide; crosslinked poly ethylene glycol of varying molecular weights from about 1K to 35K; anti-coagulates such as ethylenediamine tetraacetic acid, diethylenetriamine pentaacetic acid; 1,2-diaminocyclohexane tetra acetic acid, ehtylenebis(oxyethylenenitrilo) tetraacetic acid, and ethylenediamine tetraacetic acid disodium salt dehydrate. The preferred additional agents are selected from one or more members of the group consisting of sodium phosphate dibasic heptahydrate, potassium phosphate monobasic, sodium chloride, disodium salt dihydrate, sodium hydroxide, crosslinked poly ethylene glycol of molecular weight 20K, and ethylenediamine tetraacetic acid disodium salt dehydrate.

Further the invention includes a method for preserving cellular components comprising: obtaining a biological sample and adding a reagent comprising an effective amount of glyoxal wherein said method preserves the cellular components for a sufficient period of time. All of the aforementioned terms have the same meaning and preferred ranges. The phrase "sufficient period of time" means the time period beginning from extraction of the biological sample and ending at about 96 hours, preferably 24 to 96, hours, most preferably 24 to 72 hours. The word "preserve" means maintaining the cellular components so that they may be isolated.

Still further the invention includes a method of isolating cellular components comprising (a) obtaining a biological sample (b) adding a reagent comprising an effective amount of glyoxal (c) preserving the cellular components for a sufficient period of time, (d) isolating the cells from the biological sample, (e) extracting cellular components from such cells. All of the aforementioned terms have the same meanings and preferred ranges.

Methods of isolating cells from biological samples are known including but not limited to fluorescent-activated cell sorter, cell filtration, laser microdissection, fluorescent nanodiamonds, magnetic beads, and microfluidics. The choice of which type of isolation system should be used depends on the type of cells that are to be isolated. With respect to isolating rare cells such as CTC and CMMCs the commercial CELLSSEARCH® system may be used as well as the experimental system ("Harpoon" see WO2015/058206 entitled "Microfluidic Sorting Using High Gradient Magnetic Fields" Examples. There are a number of commercial kits and research methods that may be used to extract cellular components from biological samples that are known to scientists, including but not limited to chemical, solid phase, electrophoretic, and fluorometic techniques.

EXAMPLES

Example 1: Preparation of Preservative Solution 3

The preservative solution named as Solution 3 consists of glyoxal anti-coagulant and a cell preservative in phosphate buffer. The specific formula of preservative Solution 3 is as follows:

0.5 grams of sodium phosphate dibasic heptahydrate ($Na_2HPO_4.7H_2O$), 0.01 grams of potassium phosphate monobasic ($KH_2PO_4$), 4.1 grams of sodium chloride, 46.0 grams of ethylenediaminetetraacetic acid, disodium salt dihydrate ($Na_2EDTA.2H_2O$), 3.6 grams of crosslinked poly ethylene glycol (PEG) of 20 k molecular weight and 150 ml of glyoxal (40%) were dissolved in 800 ml of water with a mixer. After all solids were dissolved, adjusted the pH to 7.0 using sodium hydroxide and the solution final volume was then adjusted to 1000 ml by adding water. This is 30× preservative Solution 3 and 0.033 ml of preservative solution is added per ml of whole blood for the preservation of cells.

Example 2: Stability of Circulating Tumor Cells in Blood

In this example, the effect of preservative solution on preservation of circulating tumor cells (CTC) up to 96 hours was tested. Circulating tumor cells (CTC) of epithelial origin are present in the blood of carcinoma patients at very low frequency (<10/ml blood) and requires tumor cell enrichment for the detection. Positive and negative selections are two types of enrichment methods that are widely used. In positive selection, a specific marker present on rare tumor cells is used to isolate them from non-target cells in the blood. In negative selection, non-target cells are depleted from target cells in the blood. In this example, the negative selection method is used to enrich tumor cells and monitored tumor cells stability with preserved blood using the Harpoon technology. The Harpoon technology uses a chip which debulks the cells of a vacuutainer of peripheral blood by size-based removal of RBCs and platelets followed by the microfluidic inertial focusing and magnetic removal of white blood cells (WBCs) labeled with magnetic beads.

The performance of new preservative Solution 3 is compared to CellSave solution and EDTA blood without preservative. The CellSave preservative solution was developed to preserve CTCs in blood up to 96 hours in CellSearch CTC assay. The CellSearch CTC assay uses magnetic particles conjugated to anti-epithelial cell adhesion molecule (EpCAM) to enrich CTCs from 7.5 ml of blood (positive selection method).

The tissue cultured tumor cells were spiked into normal healthy blood to mimic cancer patient samples for the evaluation of preservative solution. Healthy volunteer's blood directly drawn into commercially available blood preservative tubes (CellSave, Janssen Diagnostics) or EDTA (BD Biosciences) was pooled and aliquoted into 15-ml plastic conical tubes. 33 ul of 30× preservative Solution 3 was added per ml of EDTA blood. A known number (~1000 cells/ml blood) of pre-labeled (with CytoTrack Red (CTR)) prostate tissue cultured tumor cells (Vcap) were spiked into blood samples (5.5 ml) with different preservative conditions, mixed and stored at room temperature. At 0 (~2 hrs), 24, 48, 72 and 96 hrs blood samples were processed on the Harpoon Alpha cell isolator (Janssen Diagnostics). At different time points, biotinylated cocktail antibodies ((CD45 (1.5 ug/ml final conc), CD16 (0.15 ug/ml final conc) and CD66b (0.15 ug/ml final conc)) were added to each blood sample and continuously mixed for 30 min at room temperature. After 30 min, 660 ul (120 ul/ml of blood) of Dynal Streptavidin beads were added to the blood samples and mixed for another 30 min. Blood samples treated with antibodies and Dynal beads were processed on the Alpha isolator with plastic chip 1.3v attached to mega filter or 1.3M (mega filter within the chip). Complete blood cell count was performed by Sysmex-XP300 Blood Analyzer (Sysmex Corporation) for whole blood samples before processing in the Alpha isolator system.

The product from Harpoon cell isolator which contains tumor cells were counted using Nageotte counting chamber. In brief, 400 ul of the product was stained with 1 ul of Vybrant DyeCycle Green (Life Technologies) for 5 min at RT. Pipetted 105 ul of the Vybrant DyeCycle Green stained product into one chamber of the Nageotte, then coverslip placed without disturbing the cells and allowed to settle for 2-5 minutes before counting in the Fluorescent Microscope (Nikon). The green fluorescent cells (FITC channel) counted as total (spiked tumor cells+WBCs) number of cells in the IFD product and the CTR pre-labeled spiked tumor cells as red fluorescent cells. The total number of tumor cells present in the product was calculated based on product volume. The percent recovery of tumor cells was calculated using the number of tumor cells spiked as follows:

The results from this study are shown in FIG. 1 and Table 1. FIG. 1 shows the percentage of tumor cell recovery as a function of blood storage time. As expected, the tumor cell recovery goes down from EDTA stored blood and the tumor cell recovery is 49% at 48 hour time point. There is a trend in decrease of tumor cell recovery with CellSave blood over time. However, we know that tumor cells are stable in CellSave blood based on CellSearch assay. It is possible that some of the tumor cells from CellSave blood are lost in the Harpoon Platform for reasons that are to be determined. On the other hand, there are no trends in tumor cell recovery with preservative Solution 3 and the tumor cell recovery is always above 80% up to 72 hours. The data shows that tumor cells are stable in blood preserved with preservative Solution 3 and the preserved blood is compatible with the Harpoon technology.

TABLE 1

Summary of percent tumor cell recovery with different blood preservatives.

| Time | EDTA (n = 4) | CellSave (n = 23) | Preservative Solution 3 (n = 14) | SD | SD | SD |
|---|---|---|---|---|---|---|
| 0 hr | 99.8 | 97.9 | 99.8 | 13.0 | 11.4 | 15.0 |
| 24 hrs | 72.5 | 83.6 | 89.1 | 2.7 | 12.0 | 7.7 |
| 48 hrs | 49.2 | 72.4 | 86.4 | 22.2 | 17.3 | 18.0 |
| 72 hrs | 72.5 | 65.8 | 88.0 | 19.1 | 16.6 | 14.2 |
| 96 hrs | 48.9 | 63.9 | 77.7 | 1.8 | 13.5 | 15.3 |

Example 3: RNA Recovery and Integrity from Blood Treated with Different Preservatives In addition to tumor cell enumeration, molecular characterization of tumor cells is also important for the management of cancer. However, existing fixatives preserve cells in a way that damages nucleic acids. These fixatives modify RNA/DNA through crosslinking which results in low nucleic acid yield and quality. Therefore, it is important to develop fixation methods that preserve cells as well as DNA & RNA to enable cellular and molecular analysis.

Figure 2:
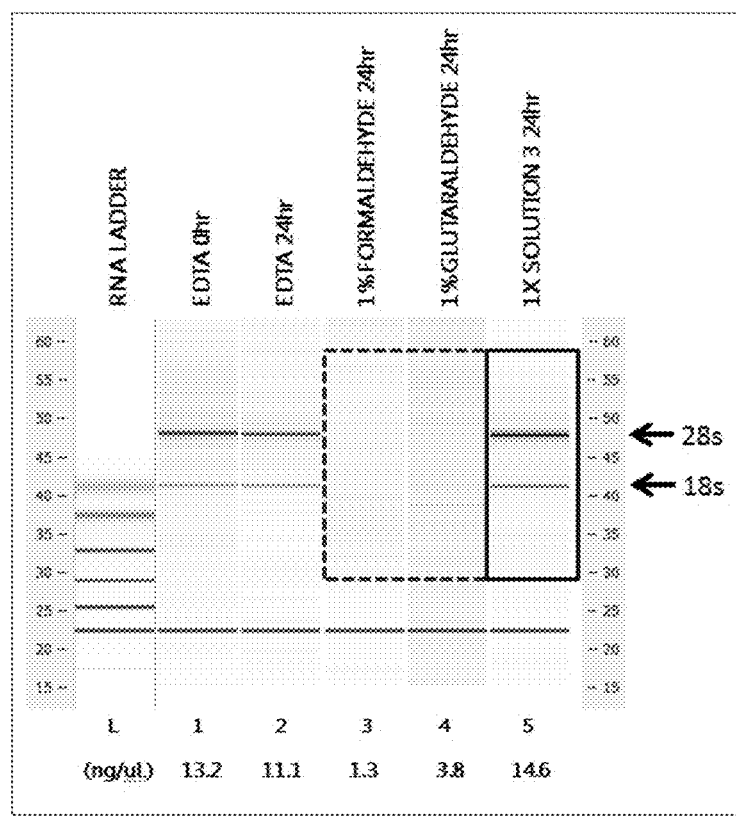
FIG. 2 shows analysis of RNA recovery and integrity by gel electrophoresis following incubation of blood with various preservatives (1% formaldehyde, 1% glutaraldehyde, Solution 3) for the indicated period of time. Blood collected into EDTA tubes without additional preservatives added is used as a control. L indicates RNA ladder control. 28S and 18S indicate position of ribosomal RNA. Amount of recovered RNA is indicated below the gel (in ng/ul).

In this example RNA recovery and its integrity from blood treated with preservatives is checked by electrophoresis. Prior to that whole blood from healthy donors was collected in EDTA tubes and exposed to various preservatives for 24 hours. RNA was extracted from samples using Qiagen Animal Blood Protection kit following manufacturer's instructions. RNA quality and quantity was assessed by running extracted RNA on Agilent 2100 Bioanalyzer. Some preservatives currently in use today fix blood cells in a manner that makes extraction of RNA (and DNA) difficult from preserved samples. Extraction becomes inefficient following preservation and integrity of recovered nucleic acids is also compromised. FIG. 2 shows that following treatment for 24 hours with 1% Formaldehyde or 1% Glutaraldehyde resulted in very poor recovery of RNA when compared to recovery obtained from samples not treated with preservatives (EDTA 0 hr and EDTA 24 hr) or samples treated for 24 hours with 1× Solution 3. Integrity of RNA recovered was also compromised following treatment with 1% Formaldehyde or 1% Glutaraldehyde when compared to EDTA controls and 1× Solution 3 treatment (note the lack of apparent bands for 28S and 18S ribosomal RNAs within dotted line box). Also note that blood samples treated with Solution 3 produced at 24 hours RNA samples of highest yield and integrity (solid black line box). This example clearly shows that treatment with Solution 3 enables recovery of higher quantity/quantity of RNA when compared to 1% Formaldehyde and 1% Glutaraldehyde. While unpreserved blood (sample EDTA 24 hr.) produced RNA of comparable quantity/quality to that obtained following treatment with Solution 3, it should be noted that only detailed analysis of expression of many individual genes is required to evaluate impact of no preservation (EDTA) on gene expression measurements. Such analysis is presented in Example 4.

Example 4: Stability of RNA Markers with Blood Preserved with Different Preservatives In this example the effectiveness of the blood preservatives is checked by monitoring the expression of a panel of genes (Table 2) in Harpoon-enriched blood samples over time.

TABLE 2

List of genes monitored during preservative formulations examinations.

| White Blood Cell Markers | | | VCaP (Prostate Cell Line) Specific Markers | House-Keeping Markers | Stress Markers |
|---|---|---|---|---|---|
| CD55 | CD14 | ITGAL | AR | ACTB | FOS |
| CD8A | CD19 | ITGAM | EPCAM | GAPDH | IL10 |
| CD8B | CD2 | PECAM1 | KLK2 | | IL1B |
| CD9 | CD24 | PTPN13 | KLK3 | | IL8 |
| CR2 | CD3D | PTPRC | KRT18 | | JUN |
| FCGR3A | CD3E | SPN | KRT19 | | TP53 |
| FUT4 | CD4 | BST1 | PSA | | |
| GYPA | CD44 | | T1E4 | | |
| IL2RA | CD5 | | TMPRSS2 | | |

The samples for RNA analysis were processed as follows. Ten-5.5 ml aliquots of EDTA and five-5.5 ml aliquots of CellSave blood were prepared from each of four healthy donors. All tubes were spiked with 500 VCAP cells. For each donor, five aliquots of EDTA blood were treated with 182 uL (33 uL/mL blood) of preservative Solution 3. One tube of blood from each donor and fixative condition (EDTA only, Solution 3, and CellSave) was processed on Harpoon alpha cell isolator immediately (t=0), and 24, 48, 72, and 96 hours after sample preparation. Output from Harpoon was centrifuged and all but ~65 ul of supernatant removed. Six hundred-fifty µl of Qiagen buffer RLT was added to the cell pellet and the samples were frozen at −80° C.

a) RNA was extracted using Qiagen All Prep RNA/DNA/ Protein Extraction kit according to manufacturer's instructions with the following modifications below:
b) Samples were thawed and two volumes ddH2O was added.
c) Proteinase K was added and the sample was incubated at 55° C. for 10 min.
d) One-half a volume of absolute ethanol was added and the sample was applied to Qiagen RNeasy Mini Columns
e) Processing continued according to the manufacturer's protocol including an on-column DNase treatment and a final elution in 30 ul water.
f) 5.0 uL (16.7% of total sample) from each sample was reverse-transcribed using the High Capacity cDNA Reverse Transcription Kit and Protocol (Life Technologies cat #: 4368814).
g) 12.5 uL of cDNA was pre-amplified using the Pre-Amplification Kit (Life Technologies cat #: 4384266) and primers for targets in the table below.
h) QPCR for the targets in the table below was performed using 3.2 uL of the pre-amplification reaction on the Fluidigm HD Biomark 96.96 Dynamic Array Chip.

Figure 3:
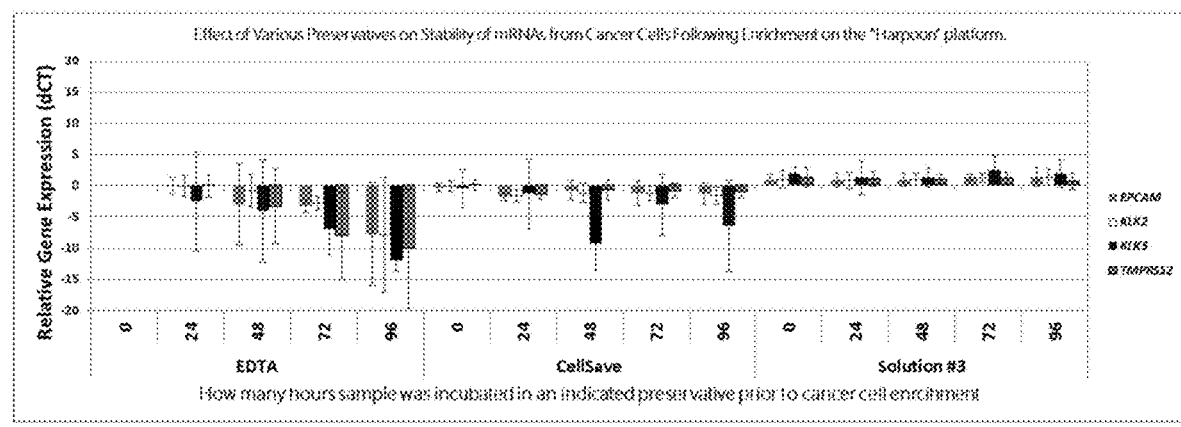
FIG. 3 shows the effect of indicated various preservatives on expression of select cancer-cell specific genes. Gene expression is presented as expression (dCT) at indicated timepoint (hr.) and treatment relative to expression in samples 0 hr. not treated with preservative (EDTA).

The results from this study are shown in FIG. 3 and Table 3. The best preservative should maintain an expression profile that is closest to the unfixed sample at baseline (EDTA 0 hr). FIG. 3 shows average relative expression value of the four donors plus/minus standard deviation for cancer cell line specific markers. Cancer specific gene levels decrease with time in blood samples collected into EDTA tubes containing additional no preservative. CellSave preservative improved RNA stability for some genes while other genes were not stabilized. The preservative Solution 3 formulation dramatically improved stability of cancer specific RNAs up to 96 hours. Variability that was seen between blood samples collected from different donors which may be due to differences in enrichment efficiency was also smallest in samples treated with Solution 3.

Table 3 shows gene expression measurements for all the genes and samples evaluated in this experiment. Cancer cell specific gene expression levels decreased with time in unfixed EDTA samples while CellSave and Preservative Solution 3 stabilized gene expression measurements. Stabilization was the best in Solution 3 and it is particularly obvious after 96 hour incubation. Some leukocyte specific genes such as CD3 and CD8 genes decrease with time in unfixed EDTA blood and CellSave preserved blood. Most leukocyte specific genes are increased relative to the EDTA 0 hr. in blood treated with preservative Solution 3. This can be explained by an observed increase in leukocyte carry over during Harpoon enrichment using blood in preservative Solution 3.

These results suggest that preservative Solution 3 prevents degradation of mRNAs present in cancer cells for up to 96 hours post blood collection. It also allows for efficient RNA recovery from treated samples. It was noted that preservative Solution 3 interferes with efficiency of white blood cell depletion on Harpoon platform. Such interference resulted in increased signal from genes expressed in white blood cells in analyzed samples. However it is important to point out that such increased signal was observed in all samples treated with mentioned novel preservative formulation and remained stable between samples processed using Harpoon platform at 0, 24, 48, 72 and 96 hours after blood collection. This again suggests that Solution 3 is very effective in preserving RNA in treated samples.

TABLE 3

Gene expression measurements for all the genes measured in samples treated with indicated preservatives for indicated periods of time. Gene expression values are calculated relative to expression at baseline, EDTA T = 0. Samples where gene expressions changed by 3 or more cycles relative to a baseline are also highlighted by ↑ or ↓ arrows.

| Gene Symbol/ Preservative-Time | | EDTA-0 | EDTA-24 | EDTA-48 | EDTA-72 | EDTA-96 | CellSave-0 | CellSave-24 | CellSave-48 | CellSave-72 | CellSave-96 | Solution #3-0 | Solution #3-24 | Solution #3-48 | Solution #3-72 | Solution #3-96 |
|---|---|---|---|---|---|---|---|---|---|---|---|---|---|---|---|---|
| Housekeeping and Leukocytes Markers | ACTB | 0.0 | −0.4 | 0.0 | −2.1 | −2.8 | 1.4 | −0.3 | 2.1 | 1.5 | 1.4 | 2.0 | 2.2 | 1.9 | 2.5 | 2.6 |
| | BST1 | 0.0 | 1.9 | 2.7 | −5.4 | −3.6 | 3.6 | −3.6 | 2.4 | −5.4 | 1.7 | 11.8 | 13.5 | 11.5 | 11.7 | 10.0 |
| | CD14 | 0.0 | 5.9 | 6.3 | 0.0 | −3.7 | 3.9 | 0.0 | 2.4 | −1.9 | 0.0 | 11.6 | 13.5 | 10.9 | 13.1 | 10.3 |
| | CD19 | 0.0 | 0.0 | 3.2 | 1.8 | 1.8 | 0.0 | 0.0 | 6.0 | 3.4 | 7.2 | 9.1 | 13.4 | 14.7 | 7.2 | 12.8 |
| | CD2 | 0.0 | −2.4 | 0.7 | −2.4 | −3.7 | −2.4 | −3.8 | 3.9 | −0.7 | 2.2 | 9.2 | 9.3 | 5.2 | 4.8 | 4.4 |
| | CD3D | 0.0 | 0.0 | 1.8 | 0.0 | 1.8 | 0.0 | 2.1 | 6.4 | 3.5 | 3.5 | 7.0 | 11.1 | 4.6 | 7.5 | 2.3 |
| | CD3E | 0.0 | 0.1 | −7.2 | −5.7 | −3.8 | −7.4 | −7.4 | −2.3 | −9.2 | −1.2 | 5.7 | 5.1 | 2.8 | 6.4 | 5.9 |
| | CD4 | 0.0 | −1.1 | −0.3 | −6.5 | −6.3 | 2.7 | −4.8 | 0.1 | −8.3 | −3.1 | 10.2 | 11.4 | 8.3 | 9.1 | 8.4 |
| | CD44 | 0.0 | −0.1 | −1.2 | −0.2 | −4.1 | 3.0 | −2.3 | 4.1 | 3.7 | 4.4 | 3.6 | 5.2 | 3.4 | 5.0 | 6.0 |
| | CD5 | 0.0 | 1.8 | 2.0 | −3.5 | 1.5 | −3.5 | −3.5 | 6.2 | −3.5 | 0.3 | −0.1 | 9.4 | 5.8 | 9.2 | 0.6 |
| | CD55 | 0.0 | 0.2 | 0.8 | −0.7 | −1.1 | 0.1 | −1.5 | 2.7 | 2.4 | 3.1 | 1.2 | 2.1 | 1.0 | 2.9 | 4.1 |
| | CD8A | 0.0 | 3.8 | 5.7 | 0.0 | 7.3 | 0.0 | −0.1 | 4.8 | 0.0 | 3.9 | 13.0 | 16.5 | 10.1 | 12.4 | 11.2 |
| | CD8B | 0.0 | −0.1 | 0.1 | −4.8 | −4.7 | −1.5 | −6.4 | 1.1 | −6.4 | 1.0 | 2.6 | 7.7 | 7.5 | 6.2 | 4.7 |
| | CD9 | 0.0 | −0.4 | −0.4 | −3.1 | −3.9 | 1.2 | −0.6 | 1.2 | 0.3 | −0.2 | 2.0 | 1.9 | 1.8 | 2.0 | 1.4 |
| | CR2 | 0.0 | 0.0 | 0.0 | 0.0 | 0.0 | 1.8 | 0.0 | 9.0 | 3.9 | 5.6 | 3.8 | 11.3 | 10.8 | 9.4 | 10.4 |
| | FCGR3B | 0.0 | 2.6 | 0.5 | −3.3 | −4.7 | 1.6 | 0.4 | 4.8 | −0.4 | −1.7 | 4.5 | 5.7 | 3.1 | 3.3 | 3.5 |
| | FOS | 0.0 | 2.1 | 5.4 | 2.0 | 1.8 | 0.8 | −0.9 | 2.5 | −0.3 | −0.1 | 1.8 | 5.9 | 1.1 | 6.1 | 5.5 |
| | FUT4 | 0.0 | −0.5 | 9.4 | 1.3 | −0.6 | 2.8 | −2.4 | 4.8 | −0.5 | −2.4 | 8.3 | 10.1 | 10.1 | 11.0 | 12.2 |
| | GAPDH | 0.0 | −0.2 | −0.6 | −2.9 | −3.7 | 0.3 | −1.3 | 1.3 | 0.0 | −0.5 | 1.7 | 2.3 | 1.4 | 1.9 | 1.7 |
| | GYPA | 0.0 | 0.4 | 2.0 | 1.8 | 2.2 | −1.6 | 0.2 | 3.4 | 5.5 | 5.8 | −1.9 | −3.2 | 2.9 | 5.2 | 6.3 |
| | IL10 | 0.0 | 0.0 | 1.6 | 0.0 | 1.4 | 1.8 | 0.0 | 4.2 | 0.0 | 0.0 | 3.3 | 8.2 | 1.6 | 3.4 | 4.3 |
| | IL1B | 0.0 | 12.6 | 14.5 | 13.0 | 11.2 | 1.8 | 4.0 | 12.5 | 4.1 | 4.7 | 11.5 | 12.5 | 10.6 | 13.3 | 12.6 |
| | IL2RA | 0.0 | 1.8 | 0.0 | 1.5 | 0.0 | 1.9 | 0.0 | 5.7 | 3.5 | 1.8 | 9.1 | 8.2 | 3.7 | 3.5 | 5.2 |
| | IL8 | 0.0 | 6.4 | 8.3 | 6.0 | 5.4 | −6.8 | −10.5 | −2.7 | −9.7 | −12.5 | 0.0 | 4.2 | −3.8 | 1.9 | 2.1 |
| | ITGAL | 0.0 | 0.3 | −0.7 | −0.4 | −2.7 | −2.5 | −5.2 | 2.5 | −7.2 | −4.6 | 3.6 | 4.7 | 2.0 | 2.2 | 2.2 |
| | ITGAM | 0.0 | 2.8 | 2.8 | 2.4 | −1.9 | −0.1 | −1.8 | 5.5 | 0.0 | −2.1 | 7.1 | 8.3 | 6.1 | 6.8 | 7.7 |
| | JUN | 0.0 | 6.7 | 4.8 | 0.9 | −0.9 | −0.7 | −2.9 | 3.2 | −4.1 | −4.2 | 6.5 | 7.6 | 6.7 | 6.9 | 3.5 |
| | PTPRC | 0.0 | 2.3 | 4.0 | 1.1 | 0.6 | 0.3 | −5.1 | 1.4 | −1.0 | −1.8 | 4.1 | 5.6 | 3.5 | 4.1 | 4.4 |
| | SPN | 0.0 | −5.2 | −0.2 | −3.8 | −2.2 | −6.3 | −7.1 | 5.1 | 3.3 | 7.5 | 7.3 | 9.0 | 7.3 | 9.2 | 11.8 |
| Cancer Cell Markers | KLK2 | 0.0 | 0.0 | −0.8 | −2.8 | −7.9 | −0.1 | −1.7 | −1.2 | −1.3 | −1.6 | 1.0 | 0.8 | 1.0 | 1.3 | 1.3 |
| | KLK3 | 0.0 | −2.6 | −4.1 | −7.0 | −12.1 | −0.5 | −1.3 | −9.3 | −3.0 | −6.5 | 1.9 | 1.3 | 1.3 | 2.4 | 1.9 |
| | KRT18 | 0.0 | −0.1 | −0.9 | −2.8 | −8.0 | −0.1 | −1.1 | 0.6 | −0.9 | −1.3 | 0.0 | 1.3 | 0.9 | 0.8 | 0.3 |
| | KRT19 | 0.0 | −2.1 | −4.3 | −4.2 | −7.5 | −1.1 | −1.9 | −0.8 | −0.8 | −2.8 | 3.6 | 0.6 | 1.0 | 1.0 | 0.5 |
| | PECAM1 | 0.0 | −0.4 | 0.2 | −4.1 | −3.7 | 1.6 | −0.3 | 2.4 | 0.6 | 0.0 | 2.6 | 2.9 | 1.8 | 1.8 | 1.4 |
| | PSA | 0.0 | −0.5 | −2.5 | −13.7 | −7.0 | 1.2 | −3.0 | −2.6 | 0.9 | −0.8 | 0.2 | 2.5 | 2.4 | 2.9 | 2.8 |
| | PTPN13 | 0.0 | −6.5 | −4.7 | −14.5 | −16.4 | −0.3 | −5.2 | 0.2 | −8.7 | −0.8 | 0.8 | 1.3 | 0.8 | 0.6 | 1.0 |

TABLE 3-continued

Gene expression measurements for all the genes measured in samples treated with indicated preservatives for indicated periods of time. Gene expression values are calculated relative to expression at baseline, EDTA T = 0. Samples where gene expressions changed by 3 or more cycles relative to a baseline are also highlighted by ↑ or ↓ arrows.

| Gene Symbol/ Preservative- Time | EDTA-0 | EDTA-24 | EDTA-48 | EDTA-72 | EDTA-96 | CellSave-0 | CellSave-24 | CellSave-48 | CellSave-72 | CellSave-96 | Solution #3-0 | Solution #3-24 | Solution #3-48 | Solution #3-72 | Solution #3-96 |
|---|---|---|---|---|---|---|---|---|---|---|---|---|---|---|---|
| T1E4 | 0.0 | -0.1 | -1.0 | -2.7 | -7.6 ↓ | -0.2 | -1.1 | -0.2 | -0.7 | -0.6 | 0.9 | 1.1 | 1.2 | 1.5 | 1.3 |
| TMPRSS2 | 0.0 | -0.1 | -3.3 ↓ | -8.0 ↓ | -10.1 ↓ | 0.1 | -1.4 | -0.7 | -0.9 | -1.0 | 1.3 | 1.1 | 1.0 | 1.1 | 0.7 |
| TP53 | 0.0 | 0.3 | -2.7 | -3.1 ↓ | -7.6 ↓ | -0.4 | -1.1 | 1.0 | -0.9 | -1.2 | 1.8 | 3.0 ↑ | 1.4 | 1.8 | 1.8 |
| AR | 0.0 | -0.2 | -1.1 | -3.2 ↓ | -6.7 ↓ | 0.0 | -1.3 | -0.8 | -0.9 | -1.7 | 1.3 | 1.1 | 1.1 | 1.1 | 0.8 |
| EPCAM | 0.0 | 0.0 | -3.0 ↓ | -3.3 ↓ | -7.8 ↓ | -0.3 | -1.8 | -0.7 | -1.2 | -1.3 | 0.9 | 0.9 | 0.9 | 1.3 | 1.4 |
| CD24 | 0.0 | 0.2 | -2.4 | -5.7 ↓ | -9.8 ↓ | -0.6 | -1.3 | 0.7 | -1.0 | -1.6 | 1.3 | 2.0 | 1.6 | 2.2 | 2.1 |

What is claimed is:

1. A reagent consisting of: (a) sodium phosphate dibasic heptahydrate; (b) potassium phosphate monobasic; (c) sodium chloride; (d) ethylenediaminetetraacetic acid, disodium salt dihydrate; (e) crosslinked polyethylene glycol (PEG) of 20 k molecular weight; and (f) an effective amount of glyoxal for preserving cells from a biological sample for subsequent isolation of cellular components.

2. The reagent of claim 1, wherein the effective amount of glyoxal is from about 0.1% to about 0.5%.

3. The reagent of claim 1, wherein the effective amount of glyoxal is about 0.2%.

4. The reagent of claim 1, wherein the cells are selected from the group consisting of circulating tumor cells (CTC), circulating melanoma cells (CMC), circulating endothelial cells (CEC), circulating multiple myeloma cells (CMMC), circulating fetal cells, antigen-specific T cells, acute myeloid leukemia stem cells, and dendritic cells.

5. The reagent of claim 1, wherein the biological sample is whole blood.

6. The reagent of claim 1, wherein the cellular components are nucleic acids.

7. The reagent of claim 1, wherein the cellular component is coding RNA.

8. The reagent of claim 1, wherein the cellular components are selected from the group consisting of mRNA, tRNA, lncRNA, rRNA, micro RNA, siRNA, snoRNA, piRNA, tsRNA, and srRNA.

9. A method for preparing a biological sample, comprising (a) contacting a biological sample comprising a plurality of cells with the reagent of claim 1; and (b) purifying one or more cells from the biological sample.

10. The method of claim 9, further comprising (c) extracting cellular components from the one or more cells purified from the biological sample.

11. The method of claim 9, wherein the effective amount of glyoxal is from about 0.1% to about 0.5%.

12. The method of claim 9, wherein the effective amount of glyoxal is about 0.2%.

13. The method of claim 9, wherein the cells are selected from the group consisting of red blood cells, white blood cells, platelets, B-Cells, T-cells, and rare cells.

14. The method of claim 13, wherein the rare cells are selected from the group consisting of circulating tumor cells (CTC), circulating melanoma cells (CMC), circulating endothelial cells (CEC), circulating multiple myeloma cells (CMMC), circulating fetal cells, antigen-specific T cells, acute myeloid leukemia stem cells, and dendritic cells.

15. The method of claim 9, wherein the biological sample is whole blood.

16. The method of claim 9, wherein the cellular components are nucleic acids.

17. The method of claim 9, wherein the cellular component is coding RNA.

18. The method of claim 9, wherein the cellular components are selected from the group consisting of mRNA, tRNA, lncRNA, rRNA, micro RNA, siRNA, snoRNA, piRNA, tsRNA, and srRNA.

19. The method of claim 9, wherein (a) contacting the biological sample with the reagent comprises preserving cellular components in the one or more cells.

20. The method of claim 9, wherein the biological sample is selected from the group consisting of bone marrow, urine, pleural effusions, saliva, lymph node fluid, and plasma.

* * * * *